US008700381B2

(12) United States Patent
Kahlman et al.

(10) Patent No.: US 8,700,381 B2
(45) Date of Patent: Apr. 15, 2014

(54) METHODS FOR NUCLEIC ACID QUANTIFICATION

(75) Inventors: Josephus Arnoldus Kahlman, Eindhoven (NL); Bin Yin, Eindhoven (NL); Tamara Nijsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 89 days.

(21) Appl. No.: 13/264,398

(22) PCT Filed: Apr. 14, 2010

(86) PCT No.: PCT/IB2010/051615
§ 371 (c)(1),
(2), (4) Date: Oct. 14, 2011

(87) PCT Pub. No.: WO2010/119407
PCT Pub. Date: Oct. 21, 2010

(65) Prior Publication Data
US 2012/0040348 A1    Feb. 16, 2012

(30) Foreign Application Priority Data
Apr. 16, 2009  (EP) .................................. 09158044

(51) Int. Cl.
*G06F 9/455* (2006.01)
*G06F 19/20* (2011.01)

(52) U.S. Cl.
CPC ..................................... *G06F 19/20* (2013.01)
USPC .......................................................... 703/23

(58) Field of Classification Search
CPC ......... G06F 19/12; G06F 19/14; G06F 19/18; G06F 19/20; G06F 19/22; G06F 19/24; G06F 19/26; G06F 19/70; G06F 9/3004
USPC .......................................................... 702/23
See application file for complete search history.

(56) References Cited

U.S. PATENT DOCUMENTS

| 6,730,501 B2 | 5/2004 | Eyre et al. |
| 2006/0009916 A1 | 1/2006 | Li et al. |
| 2006/0286587 A1 | 12/2006 | Lee et al. |
| 2007/0143385 A1 | 6/2007 | Kurnik et al. |

FOREIGN PATENT DOCUMENTS

| EP | 1138784 A2 | 10/2001 |
| WO | 2006037207 A1 | 4/2006 |
| WO | 2006048337 A1 | 5/2006 |

OTHER PUBLICATIONS

By M. W. Pfaffl:, "A New Mathematical Model for Relative Quantification in Real-Time RT-PCR" Nucleic Acids Research, Oxford University Press, Surrey, GB LNKDDOI: 10.1093/NAR/29.9.E45, vol. 29, No. 9, 1 May 2001, pp. 2002-2007, XP002330745 ISSN: 0305-1048 the whole document.

By C. Ramakers et al: "Assumption-Free Analysis of Quantitative Real-Time Polymerase Chain Reaction (PCR) Data" Neuroscience Letters, Limerick, IE LNKDDOI: 101016/S0304-3940(02) 01423-4, vol. 339, No. 1, Mar. 13, 2003, pp. 62-66, XP002330743 ISSN: 0304-3940 the whole document.

By T. Traeger et al: "High PCR Efficiency Enables More Accurate Quantification in Real-Time PCR", http://www.gene-quantification.de/qiagen-eff.pdf, Qiagen News, 2004, Issue 2, pp. 49-51.

By M. W. Pfaffl:, "Quantification Strategies in Real-Time PCR", Chapter 3, A-Z of quantitative PCR, International University Line, (IUL), La Jolla, CA, USA, publication year 2004. http://www.gene-quantification.de/chapter-3-pfaffl.pdf.

By A. Tichopad:, "Standardized Determination of Real-Time PCR Efficiency From a Single Reaction Set-Up", Nucleic Acids Research, 2003, vol. 31, No. 20, Received Jun. 24, 2003; Revised Jul. 29, 2003; Accepted Aug. 25, 2003, Oxford University Press. pp. 1-6.

*Primary Examiner* — Jerry Lin

(57) ABSTRACT

The invention relates to a method for quantification of amplified nucleic acids comprising the steps of: calculation of a measure of randomness M of the cycle-to-cycle amplification efficiency $\hat{E}(C)$ for target and comparative nucleic acids,— identification of the cycle numbers $C_M$ where M is minimal for target and comparative nucleic acids, calculation of the characteristic cycle numbers $C_c$ from the values of $C_M$.

15 Claims, 4 Drawing Sheets

METHODS FOR NUCLEIC ACID QUANTIFICATION

FIELD OF THE INVENTION

The present invention is related to the field of nucleic acid quantification by means of the polymerase chain reaction (PCR).

BACKGROUND OF THE INVENTION

Quantification of nucleic acids is important in a number of fields ranging from molecular biology and genetic research to diagnostics and pathogen detection. When sufficient amounts of nucleic acids are present blot-techniques can be applied for quantification. However, the limited sensitivity of these techniques prevents their use in a number of cases.

Quantitative PCR-methods developed in the recent past provide tools for analysis in cases where much higher sensitivity is required. These techniques are based on the fact that during PCR amplification the amount of product grows exponentially and, thus, the amount of product obtained after a comparably small number of cycles can be detected by conventional means (e.g. fluorescence detection). Further, in principle the amount of product that was present initially, i.e. at the beginning of the amplification, can be determined from the amount of product obtained at the end of the amplification if the number of amplification cycles is known.

Briefly outlined, in practice, target nucleic acids as well as standard and/or comparative samples are subjected to PCR under defined reaction conditions and formation of PCR product is monitored over the course of the amplification process. Detection of PCR product is achieved e.g. by means of fluorescently labeled hybridization probes emitting specific signals when bound to the target or by means of DNA-intercalating fluorescence dyes that allow to detect double strand product. The number of amplification cycles that are necessary to obtain a particular fluorescence threshold-level, designated as $C_t$-values, are determined and the $C_t$-value of the target is compared to the $C_t$-values of the samples of a dilution series of a nucleic acid standard with known concentration (absolute quantification). In order to determine the absolute quantity of the target a standard curve is constructed from the $C_t$-values of the standard samples and used to determine the initial concentration of the target. Alternatively, the $C_t$-value of the target is compared to the $C_t$-value of a single comparative nucleic acid of interest (relative quantification). In this case the ratio of the $C_t$-values of target and comparative sample is determined and used to assess the ratio of the initial quantities of target and comparative nucleic acid. Unfortunately, the practical application of these approaches is complicated by a number of problems, some of which will be discussed below.

Some challenges in the field of quantitative PCR are related to the growing need to analyze large numbers of samples in short intervals of time. As an ever increasing range of applications for quantitative PCR requires analysis of very large numbers of samples in a high-throughput fashion, e.g. in clinical practice, it is necessary to develop quantitative PCR-methods that can be automated completely and require very little or no human interaction. This is of crucial importance in some cases as high throughput applications (e.g. in clinical practice) simply cannot be conducted in the required short periods of time if human interaction is required.

An additional benefit that could be realized with such automated methods would be an improved comparability of analytical data between different labs currently employing widely differing laboratory protocols for quantitative PCR. The issue is of paramount importance in view of an increasing number of labs using quantitative PCR-techniques for basic research. Establishing an automated method as an objective reference for quantification experiments would drastically benefit these research efforts.

A typical plot of PCR product formed over the course of an amplification reaction reveals four different phases of the amplification process (see FIG. 1): (1) The ground phase where the fluorescence signal is dominated by background fluorescence and noise; (2) an exponential phase where the signal from PCR product rises above ground level and increases exponentially; (3) a log-linear phase where the signal increases with less than exponential rate due to decreasing amplification efficiency caused by factors as the consumption of PCR reagents and degradation of detection probes; (4) a plateau phase with marginal rise of the signal due to an increasing slowdown and ultimately stop of the amplification reaction.

Despite the seemingly straightforward concept, choosing a suitable signal-threshold level in order to determine $C_t$-values is not a simple task. As can be seen from the plot of FIG. 1 choosing a high threshold level can lead to $C_t$-values in the log-linear or plateau-phase of the amplification reaction. This is undesirable as the reaction has slowed down from exponential growth in this region obscuring the correlation between initial and present amounts of nucleic acids. Choosing a low threshold-level, on the other hand, can result in a Ct-value located in the ground phase of the amplification reaction where noise and background signal may complicate measurements. Clearly, thus, it is desirable to pick a threshold level resulting in $C_t$-values corresponding to cycles with exponential growth, i.e. in the exponential phase.

A number of approaches have been developed to achieve this goal (see e.g. J D Durtschi et al. Analytical biochemistry 2007 (361) 55-64). The basic threshold approach requires an experimenter to look at the amplification curve and use his own judgment to pick a suitable signal threshold that is crossed in the exponential phase. Since the absolute level of the signal depends on a number of factors including length of the nucleic acid and means of detection used the threshold level for this method has to be checked and, if necessary, adjusted for each application. Similarly, in the fit-point method an experimenter has to pick a suitable threshold level by his own judgment. However, instead of assigning $C_t$ to the cycle number where the recorded signal crosses the threshold, a linear fit is modeled on a semi-logarithmic plot of the exponential part of the curve and the cycle where this straight line passes the threshold is designated as $C_t$. Another concept is called the second derivative maximum method where the maximum of the second derivative of the amplification curve is determined numerically. The corresponding cycle is assumed to represent the end of the exponential growth phase, where the reaction begins to slow down to linear growth. This cycle number is used, analogously to $C_t$, for determining the quantity of the target. In contrast to the basic threshold and the fit-point method this method requires minimal or no human interaction as no threshold level has to be set by an experimenter. Yet another approach is called the sigmoidal curve-fitting method where a sigmoid function is modeled upon the amplification curve. The cycle number corresponding to the inflection point of the curve can be obtained from the model and is used, analogously to $C_t$, for determining the quantity of the target. This method, as well, requires minimal or no human interaction. The second derivative maximum method and the sigmoidal curve-fitting method, in principle, appear suitable for complete automation. The basic threshold method and the fit-point method, by nature however, require human interaction and, thus, are not suitable for automation. The second derivative maximum method and the sigmoidal curve-fitting method, however, have been found to be of limited use for applications requiring high sensitivity (J D Durtschi et al. Analytical biochemistry 2007 (361) 55-64).

It is, therefore, an object of the present invention to provide methods that are suitable for fully automated quantification of nucleic acids with high sensitivity.

OBJECTS AND SUMMARY OF THE INVENTION

This object is achieved according to the invention by a method for the relative quantification of at least one target nucleic acid in a sample comprising the steps:
(a) amplification of each of the at least one target nucleic acids contained in the sample and concurrently obtaining signals correlated to the amplification of each of the at least one target nucleic acids,
(b) amplification of each of at least one sample of comparative nucleic acids and concurrently obtaining signals correlated to the amplification of each of the at least one comparative nucleic acids,
(c) correction of the signals obtained for background signals,
(d) calculation of the cycle-to-cycle amplification efficiency $\hat{E}(C)$ for each amplification cycle of target and comparative nucleic acids,
(e) calculation of a measure of randomness M of the cycle-to-cycle amplification efficiency $\hat{E}(C)$ for target and comparative nucleic acids,
(f) identification of the cycle numbers $C_M$ where M is minimal for target and comparative nucleic acids,
(g) calculation of the characteristic cycle numbers $C_C$ from the values of $C_M$,
(h) determining the relative amounts of each of the at least one target nucleic acids in the sample in relation to the comparative nucleic acids by comparing $C_C$ of target and comparative samples.

Alternatively, this object is achieved according to the invention by a method for the absolute quantification of at least one target nucleic acid in a sample comprising the steps:
(a) amplification of each of the at least one target nucleic acids contained in the sample and concurrently obtaining signals correlated to the amplification of each of the at least one target nucleic acids,
(b) amplification of the samples of a dilution series of a nucleic acid standard with known concentration and concurrently obtaining signals correlated to the amplification of the nucleic acids in the standard samples,
(c) correction of the signals obtained for background signals,
(d) calculation of the cycle-to-cycle amplification efficiency $\hat{E}(C)$ for each amplification cycle of targets and standard samples,
(e) calculation of a measure of randomness M of the cycle-to-cycle amplification efficiency $\hat{E}(C)$ for targets and standard samples,
(f) identification of the cycle numbers $C_M$ where M is minimal for targets and standard samples,
(g) calculation of the characteristic cycle numbers $C_C$ from the values of $C_M$,
(h) determining the initial amounts of each of the at least one target nucleic acids in the sample by comparing $C_C$ of targets and standard samples.

Alternatively, this object is achieved according to the invention by a method for determining the Ct-value of at least one target nucleic acid in a sample comprising the steps:
(a) amplification of each of the at least one target nucleic acids contained in the sample,
(b) concurrently obtaining signals correlated to the amplification of each of the at least one target nucleic acids,
(c) correction of the signals obtained for background signals,
(d) calculation of the cycle-to-cycle amplification efficiency $\hat{E}(C)$ for each amplification cycle of each of the target nucleic acids,
(e) calculation of a measure of randomness M of the cycle-to-cycle amplification efficiency $\hat{E}(C)$ for each of the target nucleic acids,
(f) identification of the cycle numbers $C_M$ where M is minimal for each of the target nucleic acids,
(g) calculation of the characteristic cycle numbers $C_C$ from the values of $C_M$,
(h) calculation of $C_t$-values from the $C_C$-values.

The $C_t$-values obtained can be used for the quantification of nucleic acids with methods known in the art.

Alternatively, this object is achieved according to the invention by a method for the relative quantification of at least one target nucleic acid in a sample comprising the steps:
(a) correction of the signals obtained for amplification curves of at least one target nucleic acid and at least one comparative nucleic acid for background signals,
(b) calculation of the cycle-to-cycle amplification efficiency $\hat{E}(C)$ for each amplification cycle of target and comparative nucleic acids,
(c) calculation of a measure of randomness M of the cycle-to-cycle amplification efficiency $\hat{E}(C)$ for target and comparative nucleic acids,
(d) identification of the cycle numbers $C_M$ where M is minimal for target and comparative nucleic acids,
(e) calculation of the characteristic cycle numbers $C_C$ from the values of $C_M$,
(f) determining the relative amounts of each of the at least one target nucleic acids in the sample in relation to the comparative nucleic acids by comparing $C_C$ of target and comparative samples.

Alternatively, this object is achieved according to the invention by a method for the absolute quantification of at least one target nucleic acid in a sample comprising the steps:
(a) correction of the signals obtained for amplification curves of at least one target nucleic acid and the samples of a dilution series of a nucleic acid standard with known concentration for background signals,
(b) calculation of the cycle-to-cycle amplification efficiency $\hat{E}(C)$ for each amplification cycle of targets and standard samples,
(c) calculation of a measure of randomness M of the cycle-to-cycle amplification efficiency $\hat{E}(C)$ for targets and standard samples,
(d) identification of the cycle numbers $C_M$ where M is minimal for targets and standard samples,
(e) calculation of the characteristic cycle numbers $C_C$ from the values of $C_M$,
(f) determining the initial amounts of each of the at least one target nucleic acids in the sample by comparing $C_C$ of targets and standard samples.

Alternatively, this object is achieved according to the invention by a method for determining the Ct-value of at least one target nucleic acid in a sample comprising the steps:
(a) correction of the signals obtained for amplification curves of at least one target nucleic acid for background signals,
(b) calculation of the cycle-to-cycle amplification efficiency $\hat{E}(C)$ for each amplification cycle of each of the target nucleic acids, (c) calculation of a measure of randomness M of the cycle-to-cycle amplification efficiency Ê(C) for each of the target nucleic acids,
(d) identification of the cycle numbers $C_M$ where M is minimal for each of the target nucleic acids,
(e) calculation of the characteristic cycle numbers $C_C$ from the values of $C_M$,
(f) calculation of $C_t$-values from the $C_C$-values.

The $C_t$-values obtained can be used for the quantification of nucleic acids with methods known in the art.

Further, the present invention concerns methods as described above, which are performed in a completely automated fashion, i.e. without human interaction.

In addition, the present invention relates to machine readable media having stored thereon instructions for carrying out steps (c) to (h) of the methods described above.

Moreover, the present invention relates to an apparatus for the analysis of nucleic acid samples comprising a machine readable memory device containing information for carrying out the methods described above.

DETAILED DESCRIPTION OF THE INVENTION

Figure 1:
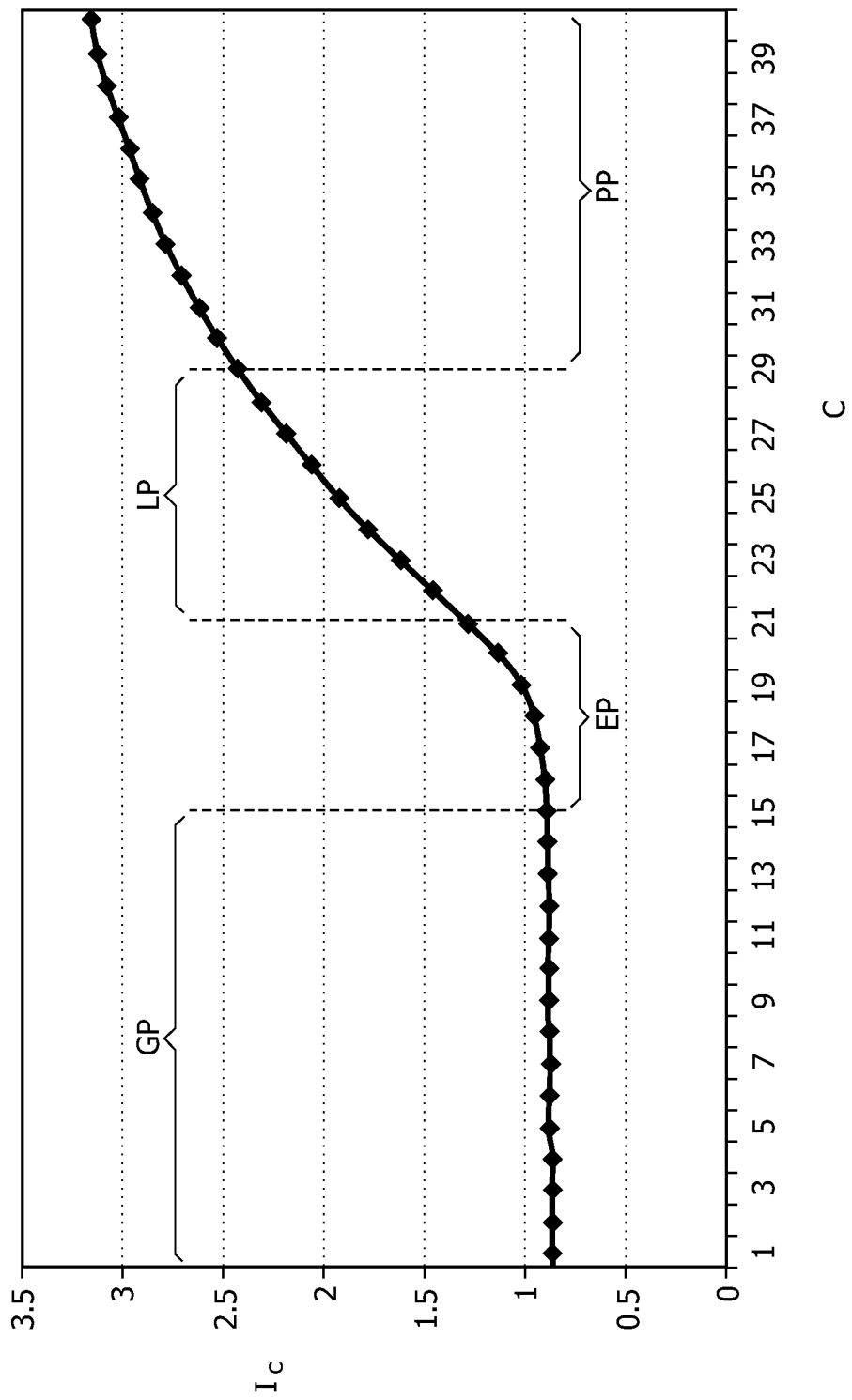
FIG. 1 shows a typical plot of PCR product formed over the course of an amplification reaction revealing different phases of the amplification process: GP=ground phase, EP=exponential phase, LP=log-linear phase, PP=plateau phase. C denotes the number of cycles and $I_C$ denotes the signal intensity recorded.

A measure of randomness of the amplification efficiency has a distinct minimum that can be used as a characteristic point of an amplification Assignment of $C_t$-values to amplification curves in the course of nucleic acid quantification using the basic threshold method or the fit-point method requires human input. Based on his own judgment the experimenter has to choose a signal threshold level that is reached before the end of the exponential phase where amplification slows down significantly and which is, further, reached after the ground phase dominated by background signal and noise. Therefore, by nature these methods are unsuitable for automation.

In contrast, the second derivative maximum method and the sigmoidal curve-fitting method involve the designation of characteristic points on the curves without human input. Therefore, in principle these methods do not appear unsuitable for automation. Recently however, the second derivative maximum method and the sigmoidal curve-fitting method were found to be unreliable for quantifying low copy numbers of target (J D Durtschi et al. Analytical biochemistry 2007 (361) 55-64).

Unexpectedly, it turned out that the plot of a measure of randomness of the amplification efficiency has a distinct minimum or a distinct transition to the minimum. The cycle number associated with this minimum or the transition to the minimum can be assigned as a characteristic point to each amplification curve without human input and can be used for reliably quantifying nucleic acids including quantification of low copy number targets.

An advantage of using the minimum or the transition to the minimum of a measure of randomness of the amplification efficiency as a characteristic point derives from the fact that this point is usually located in the early part of the exponential phase. Since amplification efficiency is influenced by various factors such as length, GC-content and potential secondary structure of the PCR product as well as inhibitors that may be present in the amplification mixture it is advantageous to use a characteristic point in the early part of the exponential phase as differences in amplification efficiency have limited impact at that stage.

Another advantage of using the minimum or the transition to the minimum of a measure of randomness of the amplification efficiency as a characteristic point derives from the fact that for a number of applications it is desirable to perform amplification of more than one species of nucleic acid in a single reaction batch. Multiplexing type of analyses (more than one target per batch) or use of internal standards can be facilitated thereby. The main advantages of these one-pot reactions are that fewer reaction batches have to be handled and that every nucleic acid in the batch is subject to the same chemical environment which may comprise inhibitors of the PCR reaction. An essential prerequisite for these one-pot analyses is that different labels have to be used for each species of nucleic acid in order to monitor amplification of each species separately. A number of different fluorescence dyes are available that can be used for this purpose at low concentrations. With increasing concentration, however, interaction of the fluorophores is likely to result in disturbance of the fluorescence signals, thus, impairing precision of the analysis. In order to minimize such an interaction of the fluorophores, therefore, it is advantageous to use a characteristic point in the early part of the exponential phase when concentrations of labeled PCR products are comparably low.

It is, therefore, another object of the present invention to provide methods for the quantification of nucleic acids, wherein the signals that are used for the quantification are signals obtained in the early part of the exponential phase of the amplification. In preferred embodiments of the present invention the early part of the exponential phase of the amplification is considered to be one of the following: The first half of the exponential phase, the first 10 cycles of the exponential phase, the first five cycles of the exponential phase, the first three cycles of the exponential phase or the first cycle of the exponential phase.

Absolute and Relative Quantification

The present invention is directed at methods for the relative quantification of nucleic acids comprising the steps:
(a) amplification of each of the at least one target nucleic acids contained in the sample and concurrently obtaining signals correlated to the amplification of each of the at least one target nucleic acids,
(b) amplification of each of at least one sample of comparative nucleic acids and concurrently obtaining signals correlated to the amplification of each of the at least one comparative nucleic acids,
(c) correction of the signals obtained for background signals,
(d) calculation of the cycle-to-cycle amplification efficiency Ê(C) for each amplification cycle of target and comparative nucleic acids,
(e) calculation of a measure of randomness M of the cycle-to-cycle amplification efficiency Ê(C) for target and comparative nucleic acids, (f) identification of the cycle numbers $C_M$ where M is minimal for target and comparative nucleic acids,
(g) calculation of the characteristic cycle numbers $C_C$ from the values of $C_M$,
(h) determining the relative amounts of each of the at least one target nucleic acids in the sample in relation to the comparative nucleic acids by comparing $C_C$ of target and comparative samples.

The present invention is, further, directed at methods for the absolute quantification of at least one target nucleic acid in a sample comprising the steps:
(a) amplification of each of the at least one target nucleic acids contained in the sample and concurrently obtaining signals correlated to the amplification of each of the at least one target nucleic acids,
(b) amplification of the samples of a dilution series of a nucleic acid standard with known concentration and concurrently obtaining signals correlated to the amplification of the nucleic acids in the standard samples,
(c) correction of the signals obtained for background signals,
(d) calculation of the cycle-to-cycle amplification efficiency $\hat{E}(C)$ for each amplification cycle of targets and standard samples,
(e) calculation of a measure of randomness M of the cycle-to-cycle amplification efficiency $\hat{E}(C)$ for targets and standard samples,
(f) identification of the cycle numbers $C_M$ where M is minimal for targets and standard samples,
(g) calculation of the characteristic cycle numbers $C_C$ from the values of $C_M$,
(h) determining the initial amounts of each of the at least one target nucleic acids in the sample by comparing $C_C$ of targets and standard samples.

The present invention is, further, directed at methods for determining the Ct-value of at least one target nucleic acid in a sample comprising the steps:
(a) amplification of each of the at least one target nucleic acids contained in the sample,
(b) concurrently obtaining signals correlated to the amplification of each of the at least one target nucleic acids,
(c) correction of the signals obtained for background signals,
(d) calculation of the cycle-to-cycle amplification efficiency $\hat{E}(C)$ for each amplification cycle of each of the target nucleic acids,
(e) calculation of a measure of randomness M of the cycle-to-cycle amplification efficiency $\hat{E}(C)$ for each of the target nucleic acids,
(f) identification of the cycle numbers $C_M$ where M is minimal for each of the target nucleic acids,
(g) calculation of the characteristic cycle numbers $C_C$ from the values of $C_M$,
(h) calculation of $C_t$-values from the $C_C$-values.

The $C_t$-values obtained can be used for the quantification of nucleic acids with methods known in the art.

The present invention is, further, directed at methods for the relative quantification of at least one target nucleic acid in a sample comprising the steps:
(a) correction of the signals obtained for amplification curves of at least one target nucleic acid and at least one comparative nucleic acid for background signals,
(b) calculation of the cycle-to-cycle amplification efficiency $\hat{E}(C)$ for each amplification cycle of target and comparative nucleic acids,
(c) calculation of a measure of randomness M of the cycle-to-cycle amplification efficiency $\hat{E}(C)$ for target and comparative nucleic acids,
(d) identification of the cycle numbers $C_M$ where M is minimal for target and comparative nucleic acids,
(e) calculation of the characteristic cycle numbers $C_C$ from the values of $C_M$,
(f) determining the relative amounts of each of the at least one target nucleic acids in the sample in relation to the comparative nucleic acids by comparing $C_C$ of target and comparative samples.

The present invention is, further, directed at methods for the absolute quantification of at least one target nucleic acid in a sample comprising the steps:
(a) correction of the signals obtained for amplification curves of at least one target nucleic acid and the samples of a dilution series of a nucleic acid standard with known concentration for background signals,
(b) calculation of the cycle-to-cycle amplification efficiency $\hat{E}(C)$ for each amplification cycle of targets and standard samples,
(c) calculation of a measure of randomness M of the cycle-to-cycle amplification efficiency $\hat{E}(C)$ for targets and standard samples,
(d) identification of the cycle numbers $C_M$ where M is minimal for targets and standard samples,
(e) calculation of the characteristic cycle numbers $C_C$ from the values of $C_M$,
(f) determining the initial amounts of each of the at least one target nucleic acids in the sample by comparing $C_C$ of targets and standard samples.

The present invention is, further, directed at methods for determining the Ct-value of at least one target nucleic acid in a sample comprising the steps:
(a) correction of the signals obtained for amplification curves of at least one target nucleic acid for background signals,
(b) calculation of the cycle-to-cycle amplification efficiency $\hat{E}(C)$ for each amplification cycle of each of the target nucleic acids,
(c) calculation of a measure of randomness M of the cycle-to-cycle amplification efficiency $\hat{E}(C)$ for each of the target nucleic acids,
(d) identification of the cycle numbers $C_M$ where M is minimal for each of the target nucleic acids,
(e) calculation of the characteristic cycle numbers $C_C$ from the values of $C_M$,
(f) calculation of $C_t$-values from the $C_C$-values.

The $C_t$-values obtained can be used for the quantification of nucleic acids with methods known in the art.

Relative quantification of nucleic acids according to the present invention refers to obtaining a quantitative measure of the ratio of the amounts of the corresponding nucleic acids in a sample before analysis.

Absolute quantification of a nucleic acid according to the present invention refers to obtaining an absolute measure of the amount of a nucleic acid in a sample before analysis, e.g. copy number or amount of substance.

Nucleic acids that are amenable to the present invention comprise DNA, RNA as well as nucleic acids with modified backbone and/or base structures. Usually amplification is performed by the polymerase chain reaction (PCR) by methods and with the aid of instrumentation available to a person of skill in the art. However, for the purpose of this invention nucleic acids that cannot be amplified by PCR directly may have to be transcribed into DNA by means known to a person of skill in the art. RNA for example may have to be transcribed into DNA before amplification using a reverse transcriptase enzyme. In order to allow reconstruction of the original amounts of the corresponding nucleic acids such a transcription process has to be performed under conditions that enable reasonably well founded assumptions concerning the ratio of the amount of nucleic acid that was transcribed into DNA and the DNA that was produced in the course of transcription. Reaction conditions of this type are well known in the art.

Each nucleic acid that is amplified in the course of practicing the present invention is usually amplified in a selective manner. One way to achieve selective amplification during PCR is the employment of specific primers. Design and use of such primers are well known to persons of skill in the art.

According to the present invention signals correlated to the amplification of nucleic acids are recorded over the course of an amplification reaction. Representation of the signals recorded over the course of all the cycles of an amplification reaction is generally denoted as the amplification curve. Usually such signals are fluorescence emissions, however, other signals employed in the art are comprised in the present invention as well. Fluorescence emissions can be released by fluorescence dyes, several of which are known in the art. Some fluorescence dyes have absorption and emission spectra that are sufficiently separated to allow parallel detection in the same sample.

For the purpose of the present invention nucleic acid amplification, i.e. the production of nucleic acids by the amplification reaction, is detected by recording signals that are correlated to the amplification of nucleic acids. This can be achieved e.g. by means of fluorescently labeled hybridization probes emitting specific signals when bound to the target or by means of DNA-intercalating fluorescence dyes that allow to detect double strand product. Such fluorescently labeled hybridization probes and DNA-intercalating fluorescence dyes are well known in the art. In a preferred embodiment of the present invention nucleic acid amplification is detected with the aid of at least one of the following: fluorescently labeled hybridization probes, FRET hybridization probes, molecular beacons, scorpion primers, Lux-primers, TaqMan probes, DNA-binding dyes.

The present invention comprises methods and means for analyzing nucleic acids. A single analysis can be directed at a single species of target nucleic acid or more than one species of target nucleic acids. In cases where more than one target nucleic acid is subject to an analysis the signals recorded to monitor the amplification of each target nucleic acid have to be distinguishable signals, i.e. signals that can be recorded at the same time separately. Methods and means to achieve such signals are well known in the art. Some fluorescence dyes for example, exhibiting absorption and emission spectra that are sufficiently separated allow parallel recording of their fluorescence signals at the same time. The present invention, thus, comprises multiplex analyses of several targets in a sample at the same time.

According to the present invention comparative nucleic acids can be used to determine reference values for the relative quantification of target nucleic acids. One or several such comparative nucleic acids can be used according to the present invention. The absolute quantity of a comparative nucleic acid in a sample before analysis does not have to be known. mRNAs of housekeeping genes in a cell for example can be used as comparative nucleic acids. In order to be amplified by PCR mRNA is usually transcribed into DNA beforehand.

According to the present invention a dilution series of a nucleic acid standard with known concentration can be used to determine reference values for the absolute quantification of target nucleic acids. Targets and diluted samples of the nucleic acid standard can be analyzed in different reaction batches or can be analyzed in one reaction batch simultaneously. If analyzed in one reaction batch simultaneously different nucleic acids and different samples of the dilution series have to be detected with distinguishable signals, i.e. signals that can be recorded at the same time separately.

In the course of practicing the present invention a background term is subtracted from the signals recorded. In order to achieve such a background correction, a linear curve is modeled on the first few cycles of the amplification curve, e.g. by linear regression. Preferably the first 10 cycles of the amplification curve are used to construct this linear curve. Alternatively, a statistical test method can be used to determine the cycles of the amplification curve that are suitable for constructing this linear curve, in particular when the signal is noisy. Subsequently, this linear curve is subtracted from the amplification curve.

According to the present invention cycle-to-cycle amplification efficiency $\hat{E}$ is calculated using:

$$\hat{E}(C)=[\tilde{I}(C+1)/\tilde{I}(C)]-1$$

wherein:
$\hat{E}$=cycle-to-cycle amplification efficiency
$C$=cycle number
$\tilde{I}$=signal intensity corrected for background signal In some embodiments of the present invention the amplification efficiency $\hat{E}$ is calculated using $\tilde{I}$-values at more than two consecutive cycles, i.e. smoothing is applied. In preferred embodiments of the present invention smoothing is applied using 3, 5 or 7 data-points.

Figure 2:
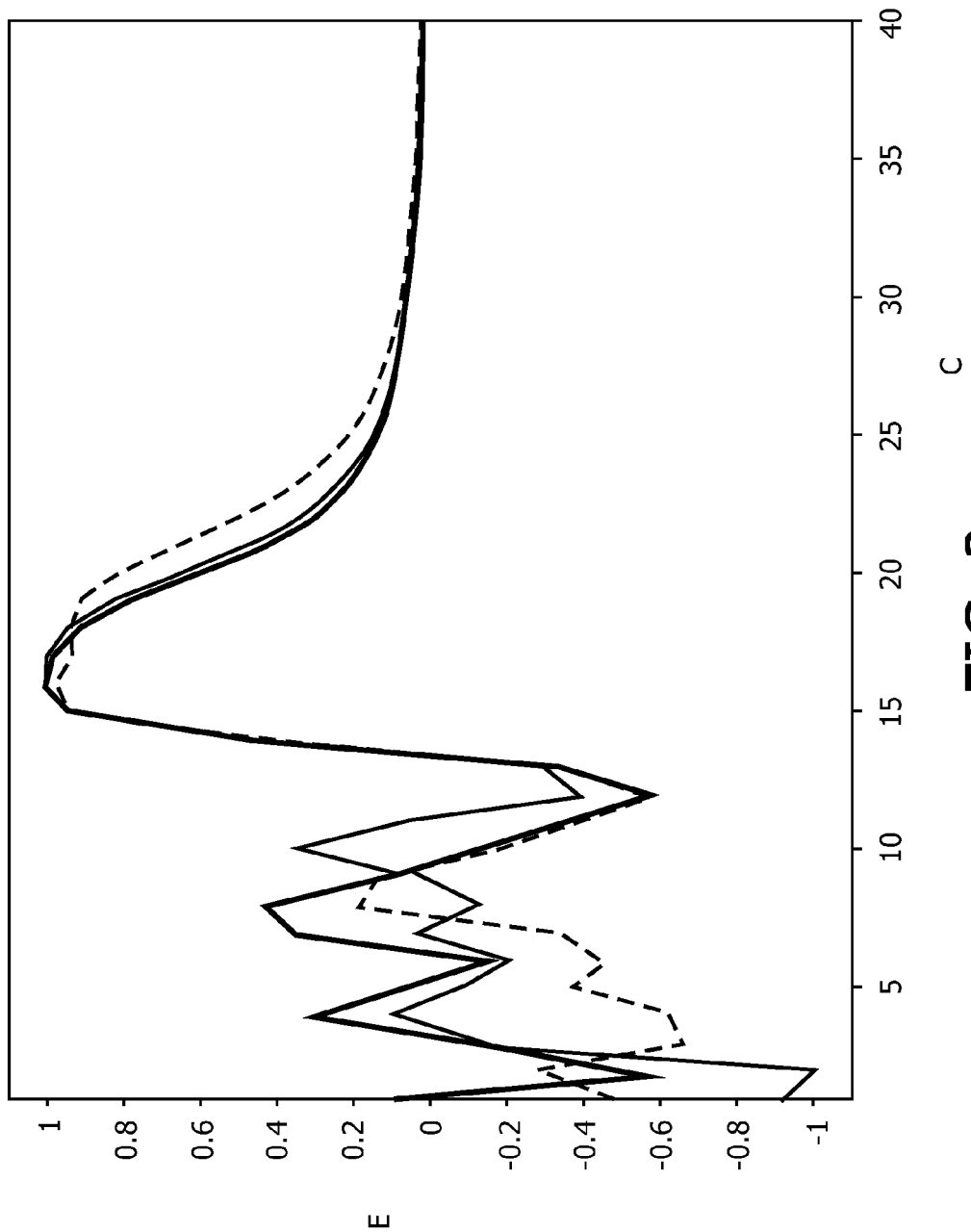
FIG. 2 shows numerically calculated Ê(C)-curves of three PCR amplifications starting with an initial amount of DNA of $10^6$ copies in a volume of 25 μl.

FIG. 2 shows numerically calculated $\hat{E}(C)$-curves of three PCR amplifications starting with an initial amount of DNA of $10^6$ copies per 25 μl.

According to the present invention a measure of randomness M of the cycle-to-cycle amplification efficiency $\hat{E}(C)$ is calculated. The spectral entropy is an example of such a measure of randomness. The spectral entropy can be calculated as follows:

(1) Form an array of $\hat{E}(C)$ as $$W(C)=[\hat{E}(C-L), \hat{E}(C-L+1), \ldots, \hat{E}(C), \ldots, \hat{E}(C+L-1), \hat{E}(C+L)]$$

where $2L+1$ is the number of $\hat{E}$ in this array that is centered at cycle C. Preferably L takes a value of 3 or 4, so W(C) has 7 or 9 elements. In order not to have an index of $\hat{E}$ smaller than one or exceeding the last available cycle number $C_{max}$ of an amplification curve, C must be within the range of $$L<C<=(C_{max}-L);$$

(2) Apply a discrete Fourier transform (DFT) on W(C) to get an array S(C) that is usually complex valued, $$S(C)=DFT\{W(C)\}=[s(1), \ldots, s(2N-1), s(2N)]$$

where 2N is the DFT size, and can be, e.g., 16 or 32;

(3) Take the modulus of S(C) and form a new array with part of its elements $$P(C)=[|s(2)|, |s(3)|, \ldots, |s(N-1)|, |s(N)|];$$

(4) Normalize the summation of the elements of P(C) to be one to get $$Pn(C)=P(C)/\text{sum}\{P(C)\}$$

where sum{ } is an array operator calculating the sum of the elements of the array;

(5) Calculate the spectral entropy (M) of the array Pn(C) as $$M(C)=\text{sum}\{Pn(C)*\log_2\{Pn(C)\}\}$$

where the multiplication * and logarithmic operation are both element wise;

(6) Update the array W(C) by centering it at cycle C+1 and repeat the steps (1)-(5).

The above method calculates the spectral entropy (M) of Ê(C) as a function of C. The smaller the spectral entropy is, the lower the degree of the randomness of the signal is.

M is characterized by a distinct minimum that is located after the ground phase and in the exponential phase of an amplification curve.

The present invention comprises embodiments where other measures of randomness are used. Examples for other measures of randomness are: (a) The residual error of polynomial curve fitting; (b) zero-crossing counting; (c) energy (RMS) calculation after high-pass filtering. All of these methods operate on the aforementioned array W(C). The former method (a) is based on the notion that a polynomial function is able to fit a deterministic function up to certain accuracy but not a stochastic one. The latter two methods ((b) and (c)) make use of the observation that noise fluctuates more than a deterministic signal around its mean value so that more zero-crossings as well as energy are generated.

According to the present invention the cycle number $C_M$ is determined where M has its minimal value. $C_M$ can be obtained numerically according to generic algorithms well known in the art. In some embodiments of the present invention the cycle number $C_M$ is determined as the cycle where M reaches its minimal for the first time.

According to the present invention the characteristic cycle numbers $C_C$ are calculated from the values of $C_M$. This calculation is performed in order to correct for the width of any windows used calculating the measure of randomness. If for example M is calculated as the spectral entropy as described above, $C_C$ is obtained from $C_M$ by subtracting L:

$$C_C = C_M - L$$

wherein L is half of the expansion of the array W(C).

Depending on the method used for calculating the measure of randomness other methods for obtaining $C_C$ from $C_M$ are apparent to a person of skill in the art. The present invention, further, comprises embodiments where the value of $C_M$ is used as the value of $C_C$, i.e. where $C_C = C_M$.

$C_C$-values can be used to calculate $C_t$-values (threshold cycle numbers) which in turn can be used for nucleic acid quantification in a manner known to a person of skill in the art (see e.g. J D Durtschi et al. Analytical biochemistry 2007 (361) 55-64). In a preferred embodiment of the present invention $C_t$-values are calculated from $C_C$-values by taking the $C_C$-values as the $C_t$-values, i.e. $C_t = C_C$.

According to the present invention determining the relative amount (R) of a target nucleic acid (T) in relation to a comparative nucleic acid (#) can be achieved by calculating:

$$R = 2^{(C_C(T) - C_C(\#))}$$

Wherein:
R=ratio of the amounts of target and comparative nucleic acid
$C_C(T) = C_C$-value for the target nucleic acid
$C_C(\#) = C_C$ value for the comparative nucleic acid Alternatively, if information regarding the amplification efficiency E is available, The Ratio R can be calculated as:

$$R = (1+E)^{(C_C(T) - C_C(\#))}$$

According to the present invention determining the initial amounts of each target nucleic acid in the sample by comparing $C_C$ of targets and standard samples can be achieved by:

Constructing a standard curve from the standard samples (initial concentrations of the standard samples versus $C_C$-values of the standard samples) and using this standard curve to derive the initial concentration of the target from the $C_C$-value of the target. The standard curve can be a linear function of $C_C$-values versus the logarithms of the concentration-values. However, alternative methods known in the art are comprised by the present invention as well.

The present invention comprises methods and means that allow to perform the methods of the invention in an automated fashion, i.e. without or with minimal human interaction. In a preferred embodiment the present invention is directed at methods and means that allow to perform the methods of the invention without human interaction. The present invention enables a person of skill in the art to use instrumentation available in the art to perform the methods of the invention without or with minimal human interaction. In a preferred embodiment the present invention enables a person of skill in the art to use instrumentation available in the art to perform the methods of the invention without human interaction.

Machine Readable Media

The present invention is directed at machine readable media having stored thereon instructions for carrying out steps (c) to (h) of the methods of the invention.

Apparatus for the Analysis of Nucleic Acid Samples

The present invention is directed at an apparatus for the analysis of nucleic acid samples comprising a machine readable memory means containing information for carrying out the methods of the invention.

EXAMPLES

Example 1

Figure 3A:
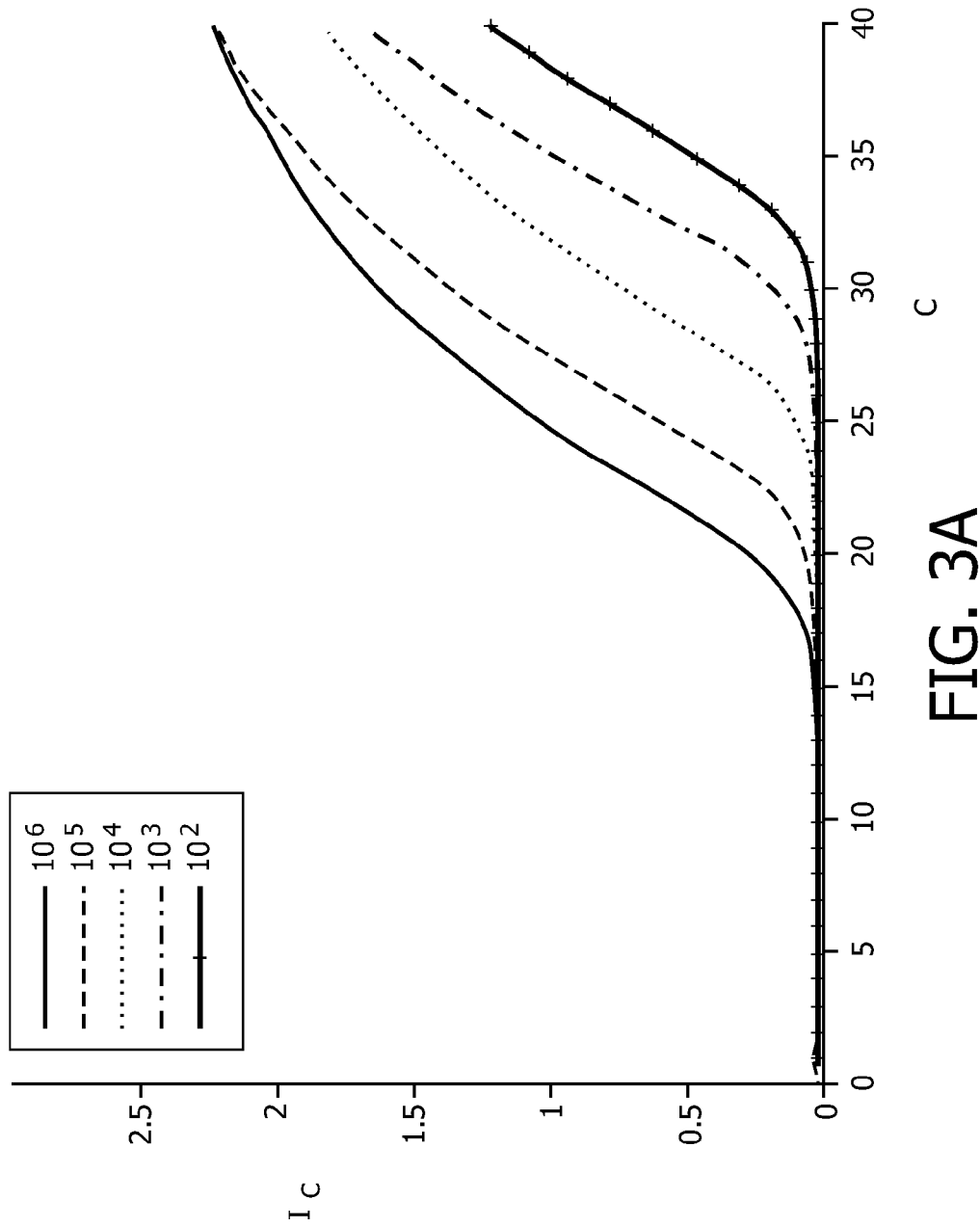
FIG. 3A shows the background corrected amplification curves obtained in example 1.
Figure 3B:
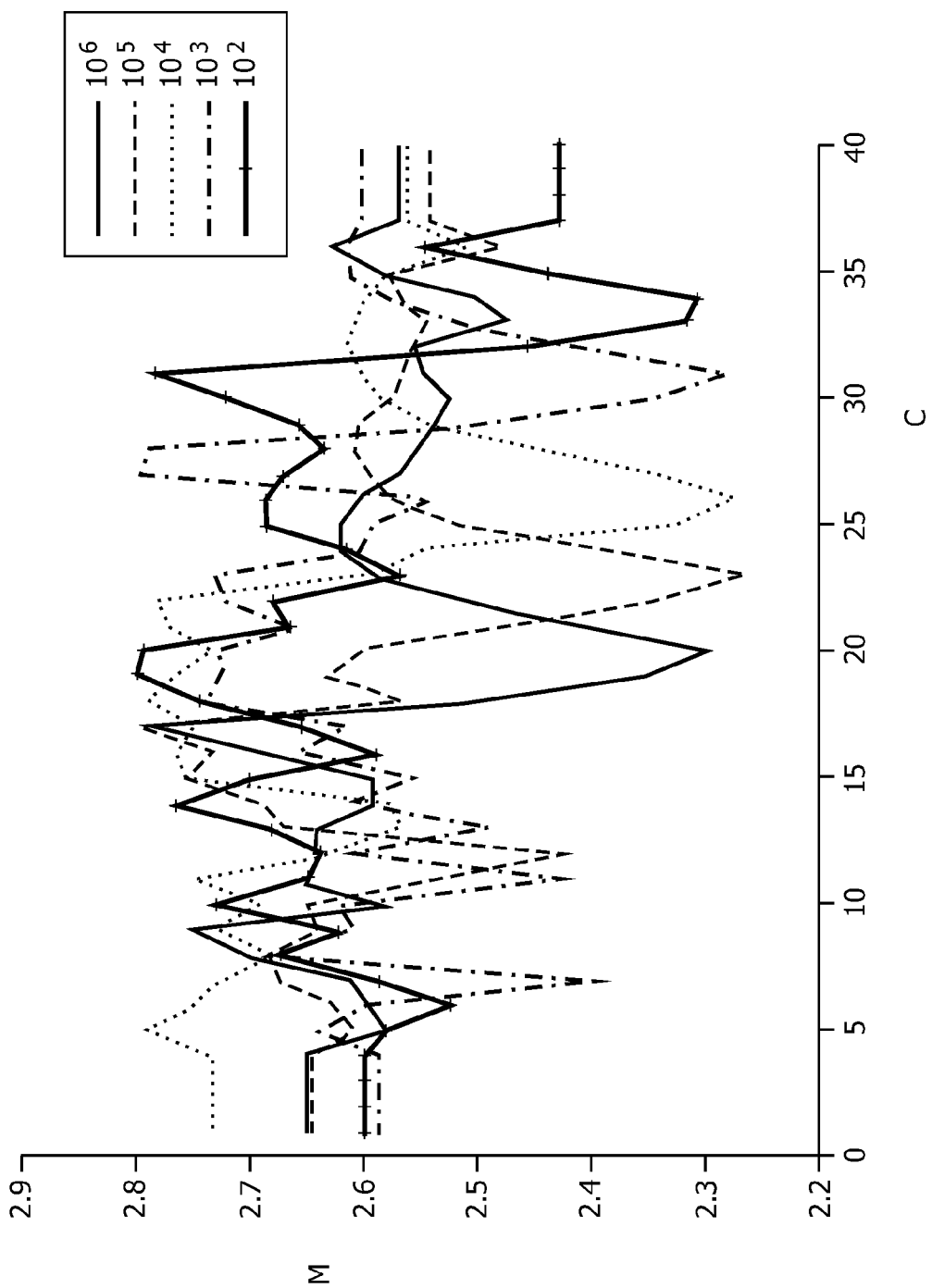
FIG. 3B shows the curves of spectral entropy obtained in example 1. The figure shows that the spectral entropy (M) displays characteristic minima at cycles (C) 20, 23, 26, 31 and 34 for the samples with concentrations of $10^6$, $10^5$, $10^4$, $10^3$, $10^2$ copies per 25 μl respectively.

DNA samples of *Staphylococcus aureus* (5' part of the 442 Sau3A1 genomic fragment, 256 basepairs, in pCR2.1-TOPO, cloned from *S. aureus* ATCC-25923) with a volume of 25 µl and concentrations of $10^6$, $10^5$, $10^4$, $10^3$, $10^2$ copies per 25 µl obtained by dilution were amplified in separate vials by 40 cycles of PCR on an ABI 7099HT version 2.3 real-time PCR cycler. For the PCR reaction Taqman Universal PCR mastermix of ABI and Taqman probes FAM-Black Hole Quencher 1 were used. Product amplification was followed. The signals obtained were corrected for background signals by modeling a linear function on the signal obtained for the first 10 cycles of PCR and subtracting this linear curve from the amplification curves obtained for each sample. FIG. 3A shows the curves that were obtained. The cycle-to-cycle amplification efficiency Ê(C) was calculated for each amplification curve using the equation $$\hat{E}(C) = [\tilde{I}(C+1)/\tilde{I}(C)] - 1$$

wherein:
Ê=cycle-to-cycle amplification efficiency
C=cycle number
Ĩ=signal intensity corrected for background signal The spectral entropy was calculated as a measure of randomness M of the cycle-to-cycle amplification efficiency Ê(C) for each amplification curve. A moving window of 9 points along the Ê(C) curve was calculated, reflecting the degree of randomness of the data points inside the window. The result is shown in FIG. 3B: The spectral entropy M displays distinct minima for the cycle-to-cycle amplification efficiency Ê(C) of each amplification reaction. The values derived for $C_M$ are 20, 23, 26, 31 and 34 for concentrations of $10^6$, $10^5$, $10^4$, $10^3$ and $10^2$ copies per 25 µl respectively. The values for $C_C$, calculated with $C_C = C_M - 4$, are thus 16, 19, 22, 27 and 30 for concentrations of $10^6$, $10^5$, $10^4$, $10^3$ and $10^2$ copies per 25 µl respectively. A linear regression of the $C_C$-values obtained against the logarithms of the respective copy numbers yielded a Pearson's coefficient of $R^2=0.9908$ indicating a good fit of the results with a linear relationship as expected.

The invention claimed is:

1. Method for the relative quantification of at least one target nucleic acid in a sample comprising the steps:
    (a) amplifying each of the at least one target nucleic acids contained in the sample and concurrently obtaining signals correlated to the amplification of each of the at least one target nucleic acids,
    (b) amplifying each of at least one sample of comparative nucleic acids and concurrently obtaining signals correlated to the amplification of each of the at least one comparative nucleic acids,
    (c) correcting the signals obtained for background signals,
    (d) calculating a cycle-to-cycle amplification efficiency $\hat{E}(C)$ for each amplification cycle of target and comparative nucleic acids,
    (e) calculating a measure of randomness M of the cycle-to-cycle amplification efficiency $\hat{E}(C)$ for target and comparative nucleic acids,
    (f) identifying cycle numbers CM where M is minimal for target and comparative nucleic acids,
    (g) calculating characteristic cycle numbers CC from values of CM,
    (h) determining relative amounts of each of the at least one target nucleic acids in the sample in relation to the comparative nucleic acids by comparing CC of target and comparative samples.

2. Method for the absolute quantification of at least one target nucleic acid in a sample comprising the steps:
    (a) amplifying each of the at least one target nucleic acids contained in the sample and concurrently obtaining signals correlated to the amplifying of each of the at least one target nucleic acids,
    (b) amplifying samples of a dilution series of a nucleic acid standard with known concentration and concurrently obtaining signals correlated to the amplifying of the nucleic acids in the standard samples,
    (c) correcting of the signals obtained for background signals,
    (d) calculating cycle-to-cycle amplification efficiency $\hat{E}(C)$ for each amplification cycle of targets and standard samples,
    (e) calculating a measure of randomness M of the cycle-to-cycle amplification efficiency $\hat{E}(C)$ for targets and standard samples,
    (f) identifying cycle numbers CM where M is minimal for targets and standard samples,
    (g) calculating characteristic cycle numbers CC from the values of CM,
    (h) determining initial amounts of each of the at least one target nucleic acids in the sample by comparing CC of targets and standard samples.

3. Method for determining the Ct-value of at least one target nucleic acid in a sample comprising the steps:
    (a) amplifying each of the at least one target nucleic acids contained in the sample,
    (b) concurrently obtaining signals correlated to the amplification of each of the at least one target nucleic acids,
    (c) correcting the signals obtained for background signals,
    (d) calculating cycle-to-cycle amplification efficiency $\hat{E}(C)$ for each amplification cycle of each of the target nucleic acids,
    (e) calculating a measure of randomness M of the cycle-to-cycle amplification efficiency $\hat{E}(C)$ for each of the target nucleic acids,
    (f) identification of cycle numbers CM where M is minimal for each of the target nucleic acids.

4. Method for the relative quantification of at least one target nucleic acid in a sample comprising the steps:
    (a) correcting signals obtained for amplification curves of at least one target nucleic acid and at least one comparative nucleic acid for background signals,
    (b) calculating a cycle-to-cycle amplification efficiency $\hat{E}(C)$ for each amplification cycle of target and comparative nucleic acids,
    (c) calculating a measure of randomness M of the cycle-to-cycle amplification efficiency $\hat{E}(C)$ for target and comparative nucleic acids,
    (d) identifying cycle numbers CM where M is minimal for target and comparative nucleic acids,
    (e) calculating characteristic cycle numbers CC from values of CM,
    (f) determining relative amounts of each of the at least one target nucleic acids in the sample in relation to the comparative nucleic acids by comparing CC of target and comparative samples.

5. Method for the absolute quantification of at least one target nucleic acid in a sample comprising the steps:
    (a) correcting signals obtained for amplification curves of at least one target nucleic acid and the samples of a dilution series of a nucleic acid standard with known concentration for background signals,
    (b) calculating cycle-to-cycle amplification efficiency $\hat{E}(C)$ for each amplification cycle of targets and standard samples,
    (c) calculating a measure of randomness M of the cycle-to-cycle amplification efficiency $\hat{E}(C)$ for targets and standard samples,
    (d) identifying cycle numbers CM where M is minimal for targets and standard samples,
    (e) calculating characteristic cycle numbers CC from the values of CM,
    (f) determining initial amounts of each of the at least one target nucleic acids in the sample by comparing CC of targets and standard samples.

6. Method according to claim 1 wherein the characteristic cycle numbers CC are defined as being equal to the corresponding CM-values (CC=CM).

7. Method according to claim 1 wherein characteristic cycle numbers CC are defined as being equal to the corresponding CM-values (CC=CM).

8. Method according to claim 1 wherein identifying includes identifying first cycle numbers CM where M reaches the minimal for target and comparative nucleic acids.

9. Method according to claim 1 wherein the measure of randomness that is calculated is selected from the group consisting of: spectral entropy, residual error of polynomial curve fitting, zero-crossing counting, energy (RMS) calculation after high-pass filtering.

10. Method according to claim 1 wherein the signals obtained are fluorescence signals.

11. Method according to claim 1 wherein nucleic acid amplification is detected with the aid of at least one of the following: fluorescently labeled hybridization probes, FRET hybridization probes, molecular beacons, scorpion primers, Lux-primers, TaqMan probes, DNA-binding dyes.

12. Method according to claim 1, wherein more than one target nucleic acids in a sample are analyzed at a same time.

13. Method according to claim 1, wherein all steps are performed in a completely automated fashion.

14. A non-transitory computer readable storage medium having stored thereon instructions for carrying out steps (c) to (h) of the method according to claim 1.

15. Apparatus for the analysis of nucleic acid samples comprising a non-transitory computer readable storage medium comprising information for carrying out the method according to claim 1.

* * * * *